(12) United States Patent
Rosenblatt et al.

(10) Patent No.: US 9,849,217 B2
(45) Date of Patent: Dec. 26, 2017

(54) ANTIMICROBIAL WRAPS FOR MEDICAL IMPLANTS

(71) Applicant: Board of Regents, The University of Texas System, Austin, TX (US)

(72) Inventors: Joel Rosenblatt, Pottstown, PA (US); Issam Raad, Missouri City, TX (US); Andrew P. Dennis, Seabrook, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/784,697

(22) PCT Filed: Apr. 17, 2014

(86) PCT No.: PCT/US2014/034556
§ 371 (c)(1),
(2) Date: Oct. 15, 2015

(87) PCT Pub. No.: WO2014/172572
PCT Pub. Date: Oct. 23, 2014

(65) Prior Publication Data
US 2016/0074559 A1    Mar. 17, 2016

Related U.S. Application Data

(60) Provisional application No. 61/813,564, filed on Apr. 18, 2013.

(51) Int. Cl.
| | |
|---|---|
| *A61L 27/54* | (2006.01) |
| *A61F 2/12* | (2006.01) |
| *A61L 27/52* | (2006.01) |
| *A61L 27/22* | (2006.01) |

(Continued)

(52) U.S. Cl.
CPC ............. *A61L 27/54* (2013.01); *A61F 2/12* (2013.01); *A61L 27/222* (2013.01); *A61L 27/502* (2013.01); *A61L 27/52* (2013.01); *A61F 2250/006* (2013.01); *A61F 2250/0018* (2013.01); *A61F 2250/0057* (2013.01); *A61F 2250/0067* (2013.01); *A61L 2300/404* (2013.01); *A61L 2430/04* (2013.01); *A61M 27/00* (2013.01)

(58) Field of Classification Search
CPC .................................. A61F 2/12; A61L 27/54
USPC ........................................................ 623/7–8
See application file for complete search history.

(56) References Cited

U.S. PATENT DOCUMENTS

| | | |
|---|---|---|
| 3,042,524 A | 7/1962 | Albus et al. |
| 4,936,858 A | 6/1990 | O'Keeffe |

(Continued)

OTHER PUBLICATIONS

PCT International Preliminary Report on Patentability issued in International Application No. PCT/US2014/034556, dated Oct. 29, 2015.

(Continued)

*Primary Examiner* — Suzette J Gherbi
(74) *Attorney, Agent, or Firm* — Parker Highlander PLLC

(57) ABSTRACT

Biodegradable antimicrobial films are provided that are solid at room temperature and substantially liquefy in situ after implantation into a mammal, such as a human patient. Methods of using the films to cover a medical device, such as a breast implant, prior to insertion into a subject are also provided.

33 Claims, 7 Drawing Sheets

(51) Int. Cl.
*A61L 27/50* (2006.01)
*A61M 27/00* (2006.01)

(56) References Cited

U.S. PATENT DOCUMENTS

| | | | |
|---|---|---|---|
| 4,984,585 A * | 1/1991 | Austad | A61B 90/02 |
| | | | 128/899 |
| 5,622,740 A | 4/1997 | Miller | |
| 5,851,229 A * | 12/1998 | Lentz | A61L 27/20 |
| | | | 623/23.64 |
| 5,931,165 A | 8/1999 | Reich et al. | |
| 6,656,488 B2 | 12/2003 | Yi et al. | |
| 6,660,827 B2 * | 12/2003 | Lentz | A61K 9/2027 |
| | | | 424/401 |
| 6,770,294 B2 | 8/2004 | Scott et al. | |
| 6,905,987 B2 * | 6/2005 | Noda | B32B 27/20 |
| | | | 428/373 |
| 7,604,817 B2 | 10/2009 | Yi et al. | |
| 7,901,702 B2 | 3/2011 | Schwarz | |
| 9,320,746 B2 * | 4/2016 | Coulter | A61K 31/223 |
| 2003/0215496 A1 * | 11/2003 | Patel | A61K 9/1617 |
| | | | 424/452 |
| 2007/0048366 A1 | 3/2007 | Chen et al. | |
| 2007/0077274 A1 | 4/2007 | Ahlers et al. | |
| 2008/0058926 A1 * | 3/2008 | Solomon | A61B 17/3468 |
| | | | 623/7 |
| 2008/0128315 A1 | 6/2008 | Buevich et al. | |
| 2008/0241212 A1 | 10/2008 | Moses et al. | |
| 2010/0254900 A1 | 10/2010 | Campbell et al. | |
| 2011/0082545 A1 * | 4/2011 | Freund | A61F 2/12 |
| | | | 623/8 |
| 2011/0082546 A1 | 4/2011 | Freund | |
| 2011/0093070 A1 * | 4/2011 | Vardi | A61B 90/02 |
| | | | 623/8 |
| 2011/0137244 A1 * | 6/2011 | Lee | A61L 31/10 |
| | | | 604/103.02 |
| 2012/0016466 A1 * | 1/2012 | Klocke | A61L 31/022 |
| | | | 623/1.42 |
| 2012/0052292 A1 | 3/2012 | Pulapura et al. | |
| 2012/0116503 A1 | 5/2012 | Grewe et al. | |
| 2012/0123535 A1 | 5/2012 | Alejandro | |
| 2013/0287836 A1 * | 10/2013 | Ingber | C08L 5/08 |
| | | | 424/443 |
| 2014/0275905 A1 * | 9/2014 | Klueh | A61L 31/10 |
| | | | 600/365 |
| 2014/0363672 A1 * | 12/2014 | Martin | A61L 17/105 |
| | | | 428/394 |
| 2015/0142098 A1 * | 5/2015 | Ruane | A61F 2/12 |
| | | | 623/1.15 |
| 2015/0239954 A1 * | 8/2015 | Quan | C07K 14/78 |
| | | | 530/354 |
| 2015/0327988 A1 * | 11/2015 | Bishop | A61B 17/06166 |
| | | | 623/8 |
| 2016/0015858 A1 * | 1/2016 | Nguyen | A61L 27/16 |
| | | | 514/180 |
| 2016/0021927 A1 * | 1/2016 | Kondo | A24D 3/061 |
| | | | 131/337 |

OTHER PUBLICATIONS

PCT International Search Report and Written Opinion issued in International Application No. PCT/US2014/034556, dated Sep. 25, 2014.

Pittet et al., "Infection in breast implants," *Lancet Infect Dis.*, 5(2):94-106, 2005.

Viola et al., "Breast tissue expander-related infections: perioperative antimicrobial regimens," *Infection Control and Hospital Epidemiology*, 35(1):75-81, 2014.

* cited by examiner

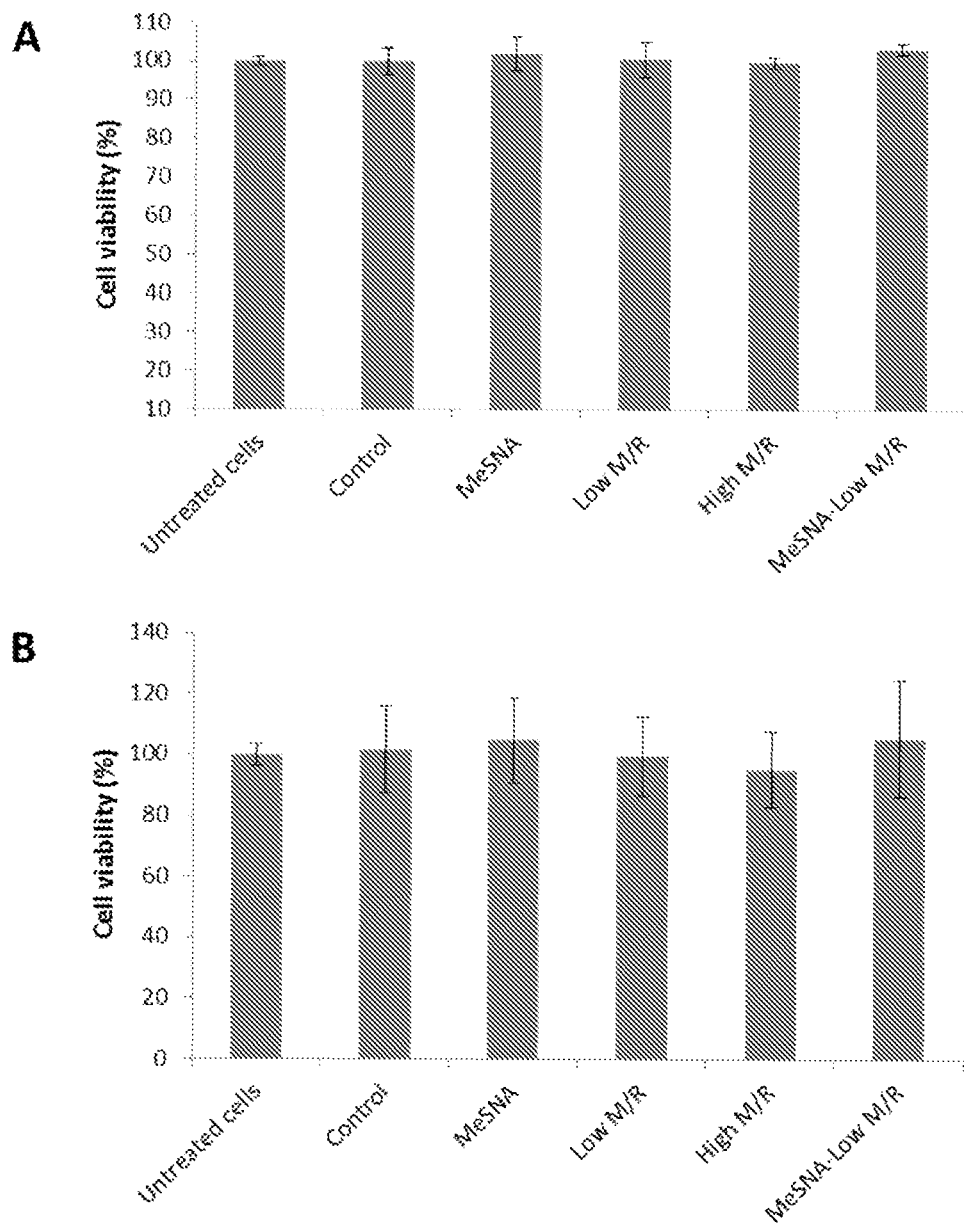
FIGS. 8A-B

ANTIMICROBIAL WRAPS FOR MEDICAL IMPLANTS

This application is a national phase application under 35 U.S.C. §371 of International Application No. PCT/US2014/034556, filed Apr. 17, 2014, which claims the benefit of U.S. Provisional Patent Application No. 61/813,564, filed Apr. 18, 2013, the entirety of each of which is incorporated herein by reference.

BACKGROUND OF THE INVENTION

1. Field of the Invention

The present invention relates generally to the field of medicine. More particularly, it concerns antimicrobial films and coverings for medical devices, and related methods.

2. Description of Related Art

Breast reconstruction is frequently performed following mastectomies. Breast implants or tissue expanders are frequently used. Infection is a significant problem associated with breast implants and tissue expanders for recovering cancer patients. Infection rates for reconstruction cases have been estimated to range from 2-24% (Pittet et al.). Other than the direct systemic complications of infection, local complications can cause discomfort, cosmesis, capsule formation and hardening and can lead to implant removal or replacement. Current protocol is to bathe breast implant and tissue expander devices in an aqueous solution of three different antibiotics for 5-15 minutes prior to insertion. Most implants are made from silicone rubber which is highly hydrophobic so the antibiotic solution rolls off the device after it is removed from the antibiotic bath, hence very little antibiotic is actually carried into the implant tissue pocket following insertion. In a retrospective study of breast implant infections following reconstructive surgery, 79% of cases had appropriate antibiotic irrigation performed prior to placement but 63% had breakthrough infections despite that (Viola et al., 2014).

Following insertion, a drainage catheter is usually left in place for a week or so which can be a conduit for bacterial access to the device. Furthermore, although the skin flap is eventually closed, breast tissue has high levels of endogenous bacterial flora that can access and colonize the device. The factors create a prolonged need for infection protection beyond the insertion procedure itself that is not met using the current standard of care. The bathing procedure adds to valuable OR time and because of the size of the implant, significant volumes of antibiotic solution are required to bathe the implant. Clearly, there is a need for methods for reducing the risk of infection associated with implanting a medical device or prosthesis, such as a breast implant.

SUMMARY OF THE INVENTION

The present invention overcomes limitations in the prior art by providing, in certain aspects, biodegradable antimicrobial films that may be wrapped around a medical implant or prosthesis, such as a breast implant, prior to insertion into a subject such as a human patient. The antimicrobial films may display a melting temperature of less than 38° C.; thus, after insertion into the subject, the film may melt and release antimicrobial agents into the immediate vicinity of the implant. In this way, increased amounts of antimicrobial agents and/or additional therapeutics may be delivered around substantially all of the surfaces of an implant. Further, since all or part of the antimicrobial film may melt in situ within several minutes, e.g., from about 1 to less than 15 minutes, which may allow for a more thorough delivery of the antimicrobial agents to the surfaces of the implant as well as improved pharmacokinetics for release of the antimicrobial agents around the medical implant. The antimicrobial agents may reduce or substantially prevent infection resulting from a bacteria or fungi. In some embodiments the biodegradable antimicrobial film comprises a highly plasticized gelatin. In various embodiments, the antimicrobial film may be subjected to dehydrothermal treatment to increase the working time and/or toughness. The plasticizer content of a highly plasticized gelatin may be adjusted to increase ductility; as shown in the below examples, increased amounts of plasticizer (e.g., 31-60% glycerol) may be included in the highly plasticized gelatin to increase the ductility. In some embodiments, the films may contain multiple layers and/or regions comprising antimicrobial compounds and regions that do not contain antimicrobial compounds.

An aspect of the present invention relates to a biodegradable covering for a medical implant, the covering comprising a highly plasticized gelatin and at least one drug to reduce infection or capsular contraction, wherein the plasticized gelatin has a melting temperature of less than about 38° C. In some embodiments, the covering may further comprise a lipid-based wax with a $T_m$ of about 27-38° C. In some embodiments, it may be possible to substitute a meltable wax with a $T_m$ of 27-38° C. for the highly plasticized gelatin. The plasticized gelatin may have a melting temperature of about 27-37° C. or 30-37° C. The plasticized gelatin may comprise about 31-60% plasticizer. The plasticizer may be glycerol, a propylene glycol, a sugar, a carbohydrate, an amino acid, a salt, an acid, or a polyol. In some embodiments, the plasticizer is glycerol. In some embodiments, at least a portion of an inner surface of the covering is substantially sticky or adhesive, and a portion of or substantially all of an outer surface of the covering is substantially lubricious. At least a portion of a surface of the covering may be treated with a gluconic acid solution. At least a portion of a surface of the covering may be treated with a glycerol-gelatin liquid comprising about 60-90% glycerol or a solution (e.g., a concentrated biodegradable solution) comprising a carbohydrate, a starch, or a sugar; such solutions may be useful for causing the portion of the surface to become substantially sticky or adhesive. The covering may be sufficient in size or shaped to cover a breast implant. The covering may be shaped as a film, a wrap, a pouch or a bag. In some embodiments, the covering is a pouch or a bag; wherein the covering has a central region and a plurality of lateral appendages, or the covering is substantially star-shaped. The covering may comprise a plurality of biodegradable layers. The at least one drug may be selected from the group consisting of an antimicrobial agent, an anti-inflammatory agent, an anti-scarring agent, a hemostatic agent, an anti-neoplastic agent, a calcium channel blocker, and a leukotriene inhibitor. The at least one drug may be comprised in a fiber, a bead, a particle, a liposome, a microsphere, or a nanosphere. The at least one drug may be an antimicrobial agent such as, e.g., bacitracin, cephalexin, gentamicin, an antiseptic, a chelator, chlorhexidine, gendine, gardine, or mixtures thereof. The antiseptic may be hydrogen peroxide, chlorhexidine, gendine, or gardine. In some embodiments, the covering further comprises mercaptoethane sulfonate (MeSNA), minocycline, rifampin, glyceryl trinitrate (GTN). The covering may further comprise a nitroglycerin or nitric oxide donor. The at least one drug may be a leukotriene inhibitor. The leukotriene inhibitor may be a leukotriene receptor antagonist selected from the group consisting of acitazanolast, iralukast, montelukast, pranlukast, verlukast, zafirlukast, and zileuton. The covering may comprise at least one, two, three, or all of mercaptoethane sulfonate (MeSNA), minocycline, rifampin, or glyceryl trinitrate (GTN). In some embodiments, the covering comprises minocycline, rifampin, and mercaptoethane sulfonate. In some embodiments, the covering further comprises glyceryl trinitrate (GTN).

In some embodiments, the covering further comprises a fatty acid or monoglyceride. The fatty acid may be a $C_{6-12}$ alkanoic acid or a $C_{6-10}$ alkanoic acid. The fatty acid may be hexanoic acid, octanoic acid, decanoic acid, dodecanoic acid, caprylic acid (octanoic acid), caproic acid, or lauric acid. In some embodiments, the fatty acid is caprylic acid (octanoic acid). The covering may further comprise glyceryl trinitrate (GTN) and capyrilic acid.

In some embodiments, at least a portion of the covering has been exposed to crosslinking. In some embodiments, at least half of the covering has been exposed to crosslinking. The crosslinking may comprise exposing at least a portion of the covering to radiation. In some embodiments, the crosslinking comprises exposing at least a portion of the covering to a dehydrothermal heat treatment. The crosslinking may be further defined as mild or partial crosslinking (e.g., incomplete crosslinking resulting from dehydrothermal heat treatment). In some embodiments, the crosslinking is sufficient to increase the working time, toughness, or stiffness of the covering. Said portion may comprise an antimicrobial agent such as, e.g., minocycline, rifampin, chlorhexidine, gendine, or gardine. In some embodiments, said portion comprises minocycline and rifampin. Said portion may further comprise mercaptoethane sulfonate (MeSNA), glyceryl trinitrate (GTN), or a $C_{6-10}$ alkanoic acid (e.g., caprylic acid).

In some embodiments, the covering comprises regions that have been exposed to crosslinking and regions that have not been exposed to crosslinking. In some embodiments, the regions that have not been exposed to crosslinking comprise the drug, and wherein the regions that have been exposed to crosslinking do not comprise the drug. In some embodiments, both the regions that have not been exposed to crosslinking and the regions that have been exposed to crosslinking both comprise the drug. In some embodiments, the regions that have not been exposed to crosslinking comprise the drug, and wherein the regions that have been exposed to crosslinking do not comprise the drug. The regions that have not been exposed to crosslinking may comprise minocycline and rifampin. In some embodiments, the regions that have not been exposed to crosslinking further comprise glyceryl trinitrate (GTN). The regions that have not been exposed to crosslinking may further comprise mercaptoethane sulfonate (MeSNA). The regions that have not been exposed to crosslinking may further comprise caprylic acid. In some embodiments, at least a portion of the covering has not been exposed to crosslinking. The covering may comprise or consist of a single layer. The covering may comprise regions that have been exposed to crosslinking and regions that have not been exposed to crosslinking. In some embodiments, the drug is comprised in the regions that have not been exposed to crosslinking. In some embodiments, the drug is comprised in the regions that have been exposed to crosslinking. The regions that have not been exposed to crosslinking may be present in the covering in a pattern of shapes or in a sponge-like pattern. The shapes may comprise a plurality of substantially circular or oval shapes (e.g., in a dotted or polka-dot pattern).

In some embodiments, the covering has multiple layers. The covering may have at least 2 layers. In some embodiments, the covering has 2 layers. In some embodiments, a layer has been exposed to crosslinking. The layer may comprise an antimicrobial agent. In some embodiments, the layer has been exposed to a dehydrothermal heat treatment and subsequently contacted with a solution containing the antimicrobial agent. The layer may be dried or exposed to a dehydrothermal heat treatment after being contacted with said solution. Said solution may comprise an alcohol (e.g., ethanol or methanol) and water. In some embodiments, the alcohol comprises about 1-50% of the solution. The solution may comprise gelatin and glycerol. In some embodiments, the covering comprises a first layer comprising a partially crosslinked plasticized gelatin and a second layer comprising a plasticized gelatin that has not been crosslinked, wherein the second layer comprises the drug. The second layer may comprise minocycline and rifampin. The highly plasticized gelatin may be comprised in an inner layer or a middle layer of the covering. In some embodiments, an outer layer of the covering has a melting temperature of greater than 38° C. The covering may have more than 2 layers, e.g., 3, 4, 5, or 6 layers. In some embodiments, the covering has 3 layers, wherein the 3 layers are an outer layer, a middle layer, and an inner layer. The outer layer of the covering may comprise said drug. The inner layer of the covering may comprise said drug. In some embodiments, the middle layer comprises the drug. The middle layer may comprise the highly plasticized gelatin. In some embodiments, the inner layer and/or the outer layer has a melting temperature of greater than 38° C. In some embodiments, the outer layer and inner layer have been exposed to crosslinking. In some embodiments, regions of the middle layer have been exposed to crosslinking and regions of the middle layer have not been exposed to crosslinking, wherein said at least one drug is comprised in a least some of the regions that have not been exposed to crosslinking. One or all of the edges of the covering may be melted or welded together. In some embodiments, the covering comprises at least three layers, and wherein the edges of the outermost layers have been melted or welded together by the application of heat. In some embodiments, the outermost layers are partially crosslinked, and wherein an inner layer comprises the highly plasticized gelatin and the drug. The inner layer may comprise minocycline and rifampin. Said application of heat may be via heat gun, food sealer, or laser. The covering may comprise minocycline and rifampin. The covering may further comprise glyceryl trinitrate (GTN). The covering may further comprises mercaptoethane sulfonate (MeSNA). The covering may further comprise caprylic acid. In some embodiments, the highly plasticized gelatin comprises (GTN and MeSNA), (GTN and caprylic acid), (MeSNA and caprylic acid), or (GTN, MeSNA, and caprylic acid); additionally, the highly plasticized gelatin may further comprise minocycline and rifampin. In some embodiments, the highly plasticized gelatin comprises (minocycline and rifampin), (minocycline, rifampin, and GTN), (minocycline, rifampin, and MeSNA), (minocycline, rifampin, GTN, and MeSNA), (minocycline, rifampin, caprylic acid, and MeSNA), or (minocycline, rifampin, GTN, caprylic acid, and MeSNA).

In some embodiments, the highly plasticized gelatin is comprised on an adhesive backing. The adhesive backing is translucent. The adhesive backing may be or comprise part of a bandage or wound dressing. In some embodiments, the highly plasticized gelatin is translucent, and wherein bandage or wound dressing allows for viewing of skin or tissue under the bandage or wound dressing. In some embodiments, the bandage or wound dressing is comprised in a kit.

Another aspect of the present invention involves a kit comprising a breast implant and a biodegradable covering of the present invention.

Yet another aspect of the present invention involves a breast implant assembly comprising a biodegradable covering of the present invention containing a breast implant.

Another aspect of the present invention relates to a method for reducing at least one post-surgical indication from breast augmentation or breast reconstruction in a subject, the method comprising surgically implanting into the subject the breast implant assembly. The biodegradable covering may be a film, and the method may further comprise wrapping the breast implant with the biodegradable covering prior to insertion. The method may further comprise trimming excess film prior to said implanting. The wrapping may occur prior to a surgery for said implantation. In some embodiments, the wrapping occurs during a surgery that comprises said implantation. The indication may be selected from the group consisting of infection, inflammation, capsular contracture, adhesion, and scarring. The biodegradable covering may be used to line or cover part or all of a region in the subjects body, wherein the breast implant is subsequently placed on the biodegradable covering, and wherein the covering is subsequently used to cover the breast implant.

Yet another aspect of the present invention relates to a transcutaneous device assembly comprising a biodegradable covering of the present invention that is wrapped around at least a portion of the transcutaneous device. The transcutaneous device may be an electrical nerve stimulation device, a catheter, a screw, a rod, a pin, a wire, a collar, a tube, or a surgical drain. In some embodiments, the transcutaneous device is a surgical drain.

Another aspect of the present invention relates to a method for reducing at least one post-surgical indication (e.g., infection, inflammation, etc.) from implantation of a transcutaneous device in a subject, the method comprising surgically implanting into the subject the transcutaneous device assembly of the present invention. The subject may be a human patient. In some embodiments, the portion of the transcutaneous device that is placed in the subject is covered by said covering. The transcutaneous device may be secured outside of the body of the subject with a wound dressing or bandage.

A variety of medical implants may be covered with a biodegradable film of the present invention. For example, the medical device may be a breast implant, a penile implant, a cosmetic restorative or enhancement implant, an implantable prosthesis, or an orthopedic implant, a dental implant, an ophthalmic implant, a cranial implant, a cardiac implant, a pump, a regulator or a stimulator.

Antimicrobial agents included in the films and wraps as described herein may inhibit the growth of or kill a wide variety of genuses and species of bacteria and fungi including, e.g., spherical, rod-shaped, and spiral bacteria. Non-limiting examples of bacteria include staphylococci (e.g., *Staphylococcus epidermidis, Staphylococcus aureus*), *Enterrococcus faecalis, Pseudomonas aeruginosa, Escherichia coli*, among other gram-positive bacteria and gram-negative bacilli. Non-limiting examples of fungal organisms include *Candida albicans* and *Candida krusei*.

A variety of therapeutic compounds may be included in the biodegradable films as disclosed herein. These compounds include antibiotics; leukotriene antagonists, such as zafirlukast, montelukast, pranlukast and zileuton; antineoplastic agents, such as 5-fluoruricil; nitric oxide producing agents, such as L-arginine; calcium-channel blockers, such as verapamil; TNF; interleukins; interferons; paclitaxel or other chemotherapy agents; 2-mercaptoethanesulfonate; antifungal agents; as well as any other agent, especially those that are known to for their ability to reduce capsular contracture. Examples of non-steroidal anti-inflammatory agents include, but are not limited to, acetaminophen, aspirin, celecoxib, diclofenac, diflunisal, flurbiprofen, ibuprofen, indomethacin, ketoprofen, ketorolac, meclofenamate, meloxicam, methyl salicylate, nabumetone, naproxen, oxaprozin, piroxicam, sulindac, tolmetin and trolamine. Examples of antimicrobial drugs include, but are not limited to: aminoglycosides, such as amikacin, gentamicin, kanamycin, neomycin, streptomycin, and tobramycin; antibiotics, such as bacitracin, clindamycin, daptomycin, lincomycin, linezolid, metronid, polymyxin, rifaximin, vancomycin; cephalosporins, such as cephazolin or cephalexin; macrolide antibiotics, such as erythromycin, azithromycin and the like; β-lactam antibiotics, such as penicillins; quinolones, such as ciprofloxacin; sulfonamides, such as sulfadiazine; tetracyclines, such as minocycline and tetracycline; and other antibiotics, such as rifampin, triclosan, chlorhexidine, gendine, and gardine.

The phrase "a chelator" denotes one or more chelators. As used herein, the term "chelator" is defined as a molecule comprising nonmetal atoms, two or more of which atoms are capable of linking or binding with a metal ion to form a heterocyclic ring including the metal ion.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 8A-B: Gelatin wrapped disks had no adverse effect on the viability of 293T cells relative to cells grown in broth. Results from Alamar blue (FIG. 8A) and MTT assays (FIG. 8B) are shown. Gelatin wrapped disks containing MeSNA, Low M/R, High M/R and MeSNA+Low M/R did not produce a significant reduction in cell viability compared to cells grown in broth.

DESCRIPTION OF ILLUSTRATIVE EMBODIMENTS

Figure 1:
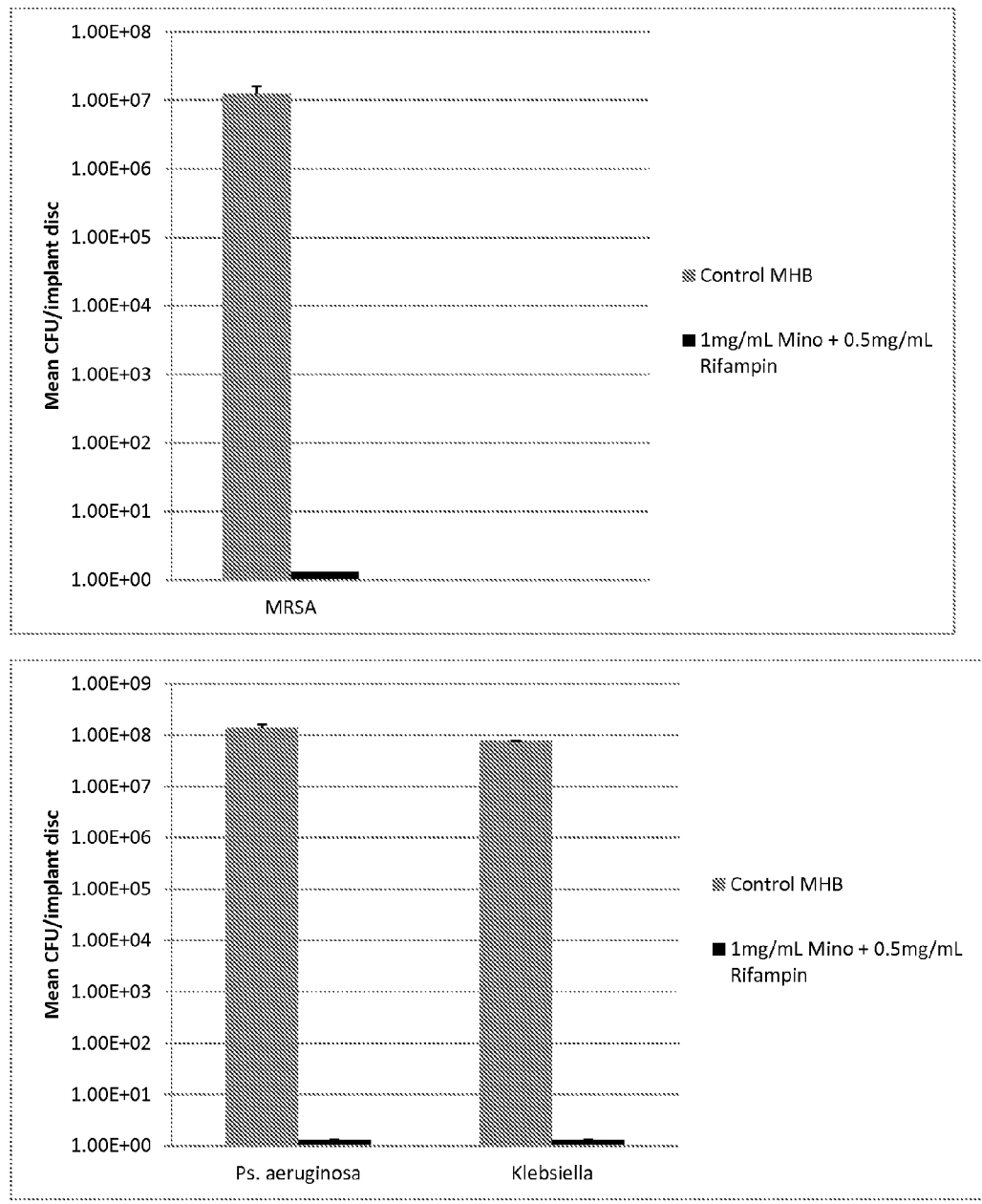
FIG. 1: Growth of test organisms on silicone discs. The presence or absence of minocycline (Mino) and rifampin (Rifampin) on silicone discs is shown.
Figure 2:
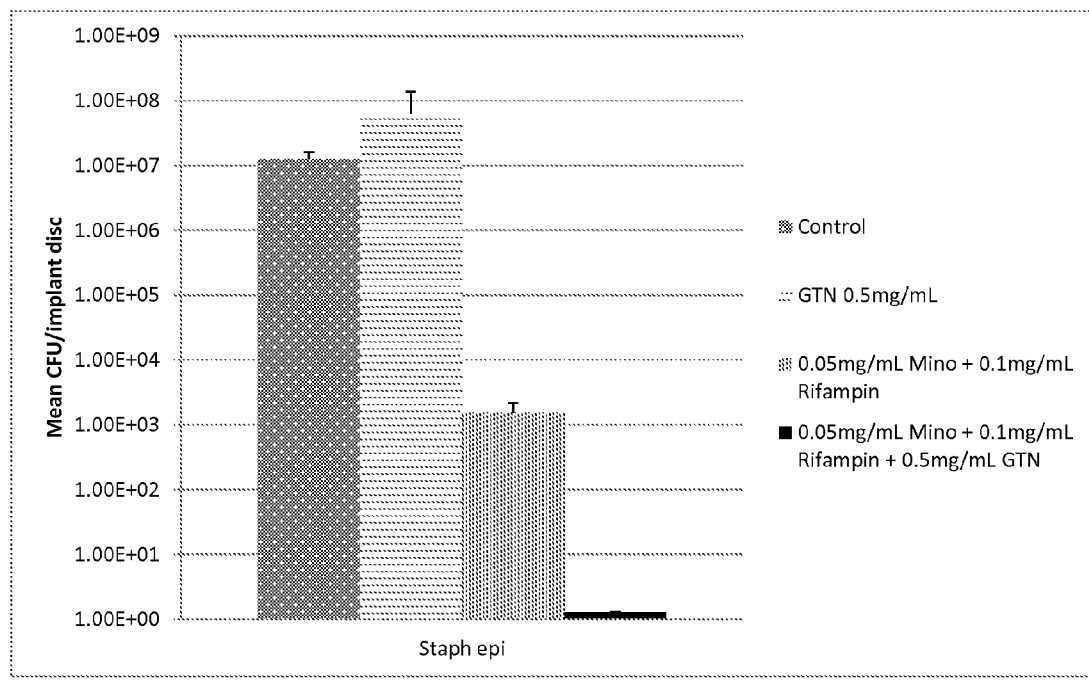
FIG. 2: Inhibition of test organisms on silicone discs with minocycline (Mino), rifampin (Rifampin), and GTN.

In some aspects, flexible solid films containing one or more antimicrobial or therapeutic agents are provided that can be wrapped around a medical implant or device prior to implantation in a mammalian subject. After implantation, the film can rapidly melt due to the temperature of the subject, e.g., to form a conformal liquid coating around the implant or device. The film may be shaped into a bag, a pouch, or a covering into which the device is inserted prior to implantation. The film may substantially melt or liquefy within minutes after implantation, e.g., about 5-20 minutes, due to the melting temperature of the film. The film generally requires sufficient mechanical strength to be able to withstand the wrapping and implantation steps without fracturing. The film can contain antimicrobial agents, analgesic agents, anti-scarring agents, anti-inflammatory agents and/or anti-fibrotic agents. The antimicrobial agents may be encapsulated in fibers or microspheres in order to extend their longevities around the implant. The film and encapsulating agents are preferably bioabsorbable. The film may be coated with an adhesive layer on one or both sides of the film. In some embodiments, the film is layered such that one side of the film is sticky or adhesive, and may facilitate adherence to the medical device, and the other side is lubricious to facilitate implantation into a tissue pocket.

Using a biodegradable antimicrobial covering or film that liquefies in situ after insertion into a mammalian subject may provide several advantages. For example, in some embodiments, such a covering may provide improved comfort immediately following implantation. A liquid coating would generally not present edges that could be irritating to soft tissues. In contrast to a solid cover which could tear or create friction from physically shifting positions within around the implant during healing, an implant that liquefies in situ after insertion may be able to substantially move within is local environment cover or alternatively the implant would not be impeded. This may be particularly important for tissue expander implants such as breast implants where the shape of the implant is changed in situ over time. Unlike previous solid shaped conformal pouches, such as those described in US20080241212, that require the manufacture of different sized solid pouches to accommodate different size devices, the liquefying films as provided herein may be produced in a single size to accommodate a wide variety of devices, e.g., by either trimming the film at the point of use or by overwrapping to form a thicker liquid coating. Applying the liquid coating as a solid for purposes of implantation can provide significant advantages, e.g., if a coating was applied as a liquid there would be a risk that it could spill off the side of the device or be scraped off or depressed into thin regions during manipulation in preparation for insertion or during the insertion process.

In some embodiments, the film or covering comprises a highly plasticized gelatin. The highly plasticized gelatin may be substantially or essentially nontoxic. The plasticized gelatin may provide advantages including, e.g., a relatively low cost, improved safety, and a predictable bioabsorption profile. In certain embodiments, the highly plasticized gelatin can be easily wrapped around an implant or tissue expanders and molded to their shape such that the device can be inserted with a conformal wrap. The wrap may melt in-situ within minutes providing a conformal liquid coating that can deliver antimicrobial (as well as other) medications to substantially all surfaces of the implant.

I. BIOABSORBABLE PLASTICIZED POLYMERS

In some embodiments, a biodegradable film or covering of the present invention comprises a bioabsorbable plasticized polymer such as, e.g., a highly plasticized gelatin. Generally, the films have a melting temperature such that they are substantially solid at room temperature, but will melt or liquefy after insertion into a mammalian subject, such as a human patient.

In some embodiments, the bioabsorbable plasticized polymer is a highly plasticized gelatin. Gelatins are protein based colloid solutions that tend to have a defined shape and allow for some movement, but typically they may be easily broken with mechanical force. In some embodiments, the strength of a gelatin is increased by introduction of a plasticizer, such as glycerol. In some embodiments, a highly plasticized gelatin may be produced as described in U.S. Pat. No. 3,042,524 or U.S. Pat. No. 5,622,740, which are incorporated by reference herein in their entirety. The plasticizing agent can increase the strength of the film and allow for the modulation of the melting temperature. In some embodiments, the addition of plasticizing agents can be used to reduce the melting temperature ($T_m$) of a plasticized gelatin to less than 38° C. (e.g., 21-38° C., 25-37.05° C., 29-37° C., etc.).

Plasticized gelatins are distinct and different from gelatin. Plasticized gelatin is displays different physical properties as compared to gelatin, including increased mechanical strength. The form of plasticized-gelatin taught in U.S. Pat. No. 5,622,740 (containing 5-30% plasticizer) is suitable for use as food casings while ordinary, non-plasticized gelatin would have been too weak and susceptible to cracking. In contrast to gelatin, plasticized-gelatin can be processed with conventional extrusion equipment. The use of conventional extrusion equipment may also provide economic advantages, as compared to gelatin, since this equipment can be used to manufacture large coverings or films.

In some embodiments, the plasticized gelatin is a highly plasticized gelatin containing a plasticizer concentration range of from greater than about 30% to about 60%. Highly plasticized-gelatin can display sufficient strength while in solid form to wrap a medical implant such as a breast implant, an ability to rapidly melt once implanted, and/or an ability to wrap and conformally adhere to a medical device. In some embodiments, the plasticized-gelatin taught in U.S. Pat. No. 5,622,740, which contain 5-30% plasticizer, are not used since these plasticized gelatins would be too stiff to wrap and conformally adhere to a medical device without some additional device such as a clip, suture or staple to secure it and prevent unwrapping. The plasticizer included in the highly plasticized gelatin may be, e.g., glycerol, a propylene glycol, a sugar, or a polyol.

Other bioabsorbable polymers with an appropriate melting temperature range may be used in various embodiments. For examples, the bioabsorbable polymer may be a caprolactone based polymer or copolymer, or a trimethylene carbonate polymer or copolymers. In other embodiments where irritation to a subject is a concern, caprolactone polymers and trimethylene carbonate polymers may be avoided, as they can degrade in vivo into acidic moieties that may cause irritation. In some embodiments, the bioabsorbable polymer may be a polyphosphazine or amino-acid based polymers. Plasticizers for these polymers include DMSO, benzyl benzoate, glycol furol, and N-methyl pyrrolidone. Certain starch and cellulose-based polymers may also be used in various embodiments. In some embodiments, the bioabsorbable polymer is a plasticized protein or polypeptide. The plasticized proteins or polypeptides may be used for forming a convertible solid film. In some embodiments the film can comprise a solid wax. In some embodiments, meltable wax compositions do not include substantial quantities of lipid-based polyols that can be metabolized to acidic moieties that become irritating inside the body; for example, Trilucent™ oil filled breast implants caused complications resulting by lipid metabolism, and were removed from the market as a result of inflammatory complications associated with metabolic conversion of lipids that leaked outside of the silicone rubber envelope of the implants. In some embodiments, the film may comprise a fatty acid such as caprylic acid. As shown herein, fatty acids such as caprylic acid may be included in a film, e.g., at a concentration of less than about 10%, to improve the antimicrobial properties of the film. fatty acids such as caprylic acid may be included in a film or antimicrobial wrap of the present invention in an amount of, e.g., less than about 10%, less than about 5%, 0.01-10%, 0.01-5%, 0.1-5%, 0.5-10%, 0.1-9%, 1-8%, 1-7%, 1-6%, or 1-5%.

Additional bioabsorbable plasticizer-polymer combinations that may be used in various embodiments are listed below.

Other Bioabsorbable Plasticizer-Polymer Combinations that May have Tm<38° C.:

| BioAbsorbable Polymer | Plasticizers |
|---|---|
| Poly lactide coglycolide | DMSO, n-METHYL 2-PYRROLIDONE, tetraglycol, glycol fural, propylene carbonate, triacetin, ethyl acetate, benzyl benzoate |
| Poly Caprolactone coglycolide | Same as above |
| Poly Caprolactone colactide | Same as above |
| Poly Dioxanone coglycolide | Same as above |
| Poly Caprolactone cotrimethylene carbonate | Same as above |

II. PLASTICIZERS

A variety of plasticizing agents may be used in various embodiments of the present invention, e.g., to alter the physical properties of and/or reduce the melting temperature of a bioabsorbable plasticized polymer. For example, plasticizing agents such as aliphatic polyols, poloxamers, sugars, and polyethylene glycols are contemplated for use in the bioabsorbable highly plasticized polymers. The plasticizer may be an amino acid or a carbohydrate. In some embodiments, the plasticizing agent is glycerol. In some embodiments, the polyols of the formula:

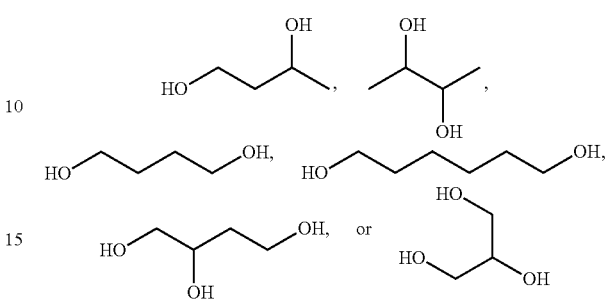

may be used. In some embodiments, the highly plasticized gelatin may arise from the combination of porcine gelatin and glycerol together. In some embodiment, the plasticizing agent can be used in percentages of approximately 30-60% of the bulk material.

As used herein, the term "highly plasticized" refers to the inclusion of from greater than about 30 to about 60% of a plasticizer in a bioabsorbable polymer. Various ranges of plasticizer may be included in a bioabsorbable polymer such as, e.g., 31-60%, 35-60%, 40-60%, or 35%, 40%, 45%, 50%, 55%, 60%, or any range derivable therein.

III. MELTING TEMPERATURES ($T_m$) OF ANTIMICROBIAL FILMS OR WRAP COMPOSITIONS

In contrast to solid biodegradable covers for medical implants that remain substantially solid or rubbery after insertion into a mammalian subject, biodegradable films or covers provided herein have, in various aspects, a melting temperature that allows for the biodegradable film or cover to remain substantially solid at room temperature (e.g., 15-25° C.), but liquefy after insertion into a mammalian subject.

This prior art does not anticipate a cover that is applied as a solid but rapidly converts into a liquid upon implantation. By rapidly we mean within a sufficient working time to implant a covered device once the implant site has been prepared. For a breast implant this typically requires several minutes.

In some aspects, the films or wrap compositions used herein may have a melting point of from about 23-36.5° C., about 24-37° C., about 25-37° C., about 30-37° C., or about 20, 21, 22, 23, 24, 25, 26, 27, 28, 29, 30, 31, 32, 33, 34, 35, 36, 37, or 38° C., or any range derivable therein. In addition to the melting temperature, the rate of liquefaction of the film or wrap (i.e., the rate at which the material liquefies) can also be affected by the degree of hydration of the material. For example, the wrap of film may require hydration for liquefaction; thus, if the wrap or film is more dehydrated (e.g., via a dehydrothermal heat treatment), then the film or wrap may hydrate more slowly and thus liquefy more slowly. The hydrophilicity of the plasticizer or the hydrophilicity of bioactive or antimicrobial agents present in the film or wrap may affect the degree of hydration and/or the rate of hydration of the material after inserted in a subject. Additionally, increased amounts of crosslinking, such as dehydrothermal heat treatment, can make the film tougher and slow the rate of liquefaction by removing more water from the film or wrap, thus slowing the liquefaction of the film or wrap after insertion into a subject, such as a human patient. In some embodiments, the melting or liquefaction of a film or wrap of the present invention may take at least 5, 10, 15, 20, 25, 30, 35, 40, 45, 50, 55, or at least 60 minutes after insertion onto or into a mammalian subject, such as a human patient.

The melting point ($T_m$) of a compound is distinct and different from the glass transition temperature ($T_g$) of a compound. There are several ways to describe the change in ordered structure of a compound and the temperature upon which that substance undergoes changes. The classic description of a melting temperature ($T_m$) relates specifically to the changing of a substance which goes from one phase to another, specifically from a solid phase to a liquid phase. On the other hand, the glass transition temperature ($T_g$) describes the conversion of an amorphous solid from a brittle solid into a more free flowing or rubbery glass. While a glass transition temperature can be near to the melting temperature, the glass transition temperature is almost always lower than the melting temperature. Finally, the glass transition temperature does not relate to a true phase transition like a melting temperature rather represents a series of different possible changes in properties such as viscosity of a polymer. Restated, although the glass transition temperature of the compound may be lower than 38° C., the melting temperature of the compound may not be below that threshold.

IV. ADDITIONAL THERAPEUTIC AGENTS

One or more additional therapeutic agent may be included in an antimicrobial film or pouch of the present invention. The therapeutic agent may be an antimicrobial agent, an anesthetic, an analgesic, an anti-inflammatory agent, an anti-scarring agents, an anti-fibrotic agent, an anti-neoplastic agent, and/or a leukotriene inhibitor.

Therapeutic or bioactive agents may be incorporated into a film or cover of the present invention in a variety of ways. For example, one or more therapeutic agent may be dissolved or emulsified in the plasticizing liquids of the invention, e.g., to ensure a substantially even dispersal, and then the therapeutic agent(s) may be incorporated during the formation or synthesis of the film or cover. Alternatively, they could be suspended in a solid composition prior to forming and solidifying the films. In some embodiments, a therapeutic agent may be first encapsulated in fibers, beads, particles, liposomes, microspheres or nanospheres and then dispersed into a film or coating as described herein. In some embodiments, biodegradable microspheres, biodegradable nanospheres, or phospholipid liposomes may be utilized. The encapsulating polymers are preferably bioabsorbable. In some embodiments, the encapsulating polymers may degrade or absorb into the surrounding tissues at a different rates than the film, e.g., to prolong or reduce the rate of release of the therapeutic agent(s) into the surrounding tissues. The bioactive agent may also be applied as a thin mesh on top of or between film layers in a multilayer film by a variety of processes including nanospinning. Bioactive agents of interest include antimicrobial agents, particularly combinations of minocycline and rifampin and other antimicrobials, gendine based combinations, and combinations of antimicrobials with nitroglycerin or nitric oxide donors. A chelator may be included in a bioabsorbable film of the present invention. In addition to antimicrobial agents, an analgesic agent (e.g., lidocaine), an antiscarring agents (e.g., MeSNA), an anti-inflammatory agent (e.g., a steroid), an efflux pump inhibitor (e.g., Verapamil), or an antifibrotic agent (e.g., a TGF-beta inhibitor) may be included in the bioabsorbable film.

In some embodiments, a therapeutic agent as described in US20080241212, US2008128315, US20120052292, US20110082545, US20110082546, or US20120123535, which are incorporated herein in their entirety, may be included in a biodegradable film, pouch, sleeve, or covering, e.g., to for covering a breast implant, of the present invention.

The therapeutic agent may be an antimicrobial agent such as a rifamycin (e.g., rifampin, rifamycin, rifampicin) and/or a tetracycline antibiotic such as minocycline. In some embodiments, the bioabsorbable film may comprise rifampin and minocycline. As shown in the below examples, inclusion of a nitroglycerin or nitric oxide donors, such as glyceryl trinitrate (GTN) may result in a synergistic enchantment of the antimicrobial or bactericidal effects of antibiotics (e.g., minocycline and rifampin). Inclusion of MeSNA of capyrilic acid may also result in a significant or synergistic improvement in the antimicrobial effects of minocycline and rifampin. The bioabsorbable film or covering may further comprise an antifungal agent or an antiviral agent.

In some embodiments, a nitroglycerin or nitric oxide donor is included in the bioabsorbable film. For example, the nitroglycerin or nitric oxide donor may be glyceryl trinitrate (GTN), L-arginine, mono- or dinitrate (such as glycerol mono or dinitrate), nitrosocompound (such as nitrosoglutathione or nitrosocycteine), isosorbide nitrate (such as isosorbide di- or mono-nitrate), a nitroprusside, a diazenium diolate (such as NONOates), a nitric oxide complex (such as nitric oxide-spermine), or an exogenous nitric oxide generating catalyst (such as reduced silver, copper and other metal ions).

A variety of antibacterial agents may be included in the bioabsorbable film. The antimicrobial agent may be an antibacterial agent. Antibacterial agent that may be used include, e.g., aminoglycosides, beta lactams, quinolones or fluoroquinolones, macrolides, sulfonamides, sulfamethaxozoles, tetracyclines, streptogramins, oxazolidinones (such as linezolid), clindamycins, lincomycins, rifamycins, glycopeptides, polymxins, and lipo-peptide antibiotics. The antibacterial agent may be formulated, e.g., as a pharmacologically acceptable salt, in a lipid formulations, etc. Exemplary aminoglycosides that may be used in some specific aspects of the invention include amikacin, kanamycin, gentamicin, tobramycin, or netilmicin. Beta lactams are a class of antibacterials that inhibit bacterial cell wall synthesis. A majority of the clinically useful beta-lactams belong to either the penicillin group (penam) or cephalosporin (cephem) groups. The beta-lactams also include the carbapenems (e.g., imipenem), and monobactams (e.g., aztreonam). Inhibitors of beta-lactamase such as clavulanic acid and its derivatives are also included in this category. Non-limiting examples of the penicillin group of antibiotics that may be used in the solutions of the present invention include amoxicillin, ampicillin, benzathine penicillin G, carbenicillin, cloxacillin, dicloxacillin, piperacillin, or ticarcillin, etc. Examples of cephalosporins include ceftiofur, ceftiofur sodium, cefazolin, cefaclor, ceftibuten, ceftizoxime, cefoperazone, cefuroxime, cefprozil, ceftazidime, cefotaxime, cefadroxil, cephalexin, cefamandole, cefepime, cefdinir, cefriaxone, cefixime, cefpodoximeproxetil, cephapirin, cefoxitin, cefotetan etc. Other examples of beta lactams include mipenem or meropenem which are extremely active parenteral antibiotics with a spectrum against almost all gram-positive and gram-negative organisms, both aerobic and anaerobic and to which *Enterococci, B. fragilis*, and *P. aeruginosa* are particularly susceptible. Examples of beta lactamase inhibitors include clavulanate, sulbactam, or tazobactam. Exemplary macrolides include erythromycin, azithromycin, clarithromycin. Examples of quinolones and fluoroquinolones include nalidixic acid, cinoxacin, trovafloxacin, ofloxacin, levofloxacin, grepafloxacin, trovafloxacin, sparfloxacin, norfloxacin, ciprofloxacin, moxifloxacin and gatifloxacin. Exemplary sulphonamides include mafenide, sulfisoxazole, sulfamethoxazole, and sulfadiazine. The tetracycline group of antibiotics include tetracycline derivatives such as tigecycline, minocycline, doxycycline, demeclocycline, anhydrotetracycline, chlorotetracycline, and epioxytetracycline. The streptogramin antibacterial agents include quinupristin and dalfopristin. Other antibacterial drugs include glycopeptides such as vancomycin and teicoplanin. Other antibacterial drugs include polymyxins, such as colistin, prestinomycin, chloramphenicol, trimethoprim, fusidic acid, metronidazole, bacitracin, spectinomycin, nitrofurantion, daptomycin or other leptopeptides, oritavancin, dalbavancin, ramoplamin, and ketolide A variety of chelators may be included in a bioabsorbable film as disclosed herein. Exemplary chelators include EDTA free acid, EDTA 2Na, calcium disodium EDTA, EDTA 3Na, EDTA 4Na, EDTA 2K, EDTA 2Li, EDTA 2NH$_4$, EDTA 3K, Ba(II)-EDTA, Ca(II)-EDTA, Co(II)-EDTACu(II)-EDTA, Dy(III)-EDTA, Eu(III)-EDTA, Fe(III)-EDTA, In(III-EDTA, La(III)-EDTA, CyDTA, DHEG, diethylenetriamine penta acetic acid (DTPA), DTPA-OH, EDDA, EDDP, EDDPO, EDTA-OH, EDTPO, EGTA, HBED, HDTA, HIDA, IDA, Methyl-EDTA, NTA, NTP, NTPO, O-Bistren, TTHA, EGTA, DMSA, deferoxamine, dimercaprol, zinc citrate, a combination of bismuth and citrate, penicillamine, succimer or Etidronate. The chelator may bind barium, calcium, cerium, cobalt, copper, iron, magnesium, manganese, nickel, strontium, or zinc.

V. PATTERNED AND/OR LAYERED FILMS AND COVERINGS

In some embodiments, an antimicrobial covering or film of the present invention comprises regions that contain antimicrobial compounds and regions that do not contain antimicrobial compounds. The antimicrobial covering or film may comprise 2, 3, 4, or more layers. In some embodiments, the antimicrobial covering or film may contain 2 or more layers, wherein some layers contain antimicrobial compounds and other layers do not contain antimicrobial compounds. For example, in some embodiments, the film may comprise three layers including two outer layers that do not contain antimicrobial compounds and a middle layer that contains one or more antimicrobial compound(s) (e.g., minocycline, rifampin, GTN, MeSNA, and/or caprylic acid; minocycline and rifampin; minocycline, rifampin, and GTN; minocycline, rifampin, and MeSNA; minocycline, rifampin, MeSNA, and caprylic acid) that are either continuously distributed throughout the middle layer or contained in regions of the middle layer. In some embodiments, the outer layers of a layered film may have either higher melting temperatures and/or improved handling properties. In some embodiments, it may be desirable to include the antimicrobial compound(s) the outer layers of a layered film or covering. As would be appreciated by one of skill in the art, the pattern of distribution of antimicrobial compounds in regions of a film or layer of film may be selected as desired; for example, the regions may be roughly circular or oval (e.g., in a "polka-dot" pattern), square, striped, etc., as desired. In some embodiments, an antimicrobial film or antimicrobial layer of film may contain the antimicrobial compounds distributed throughout the layer in a sponge-like pattern based on the creation of voids in the film that are subsequently filled with a filler (e.g., containing or consisting of a highly plasticized gelatin) comprising the antimicrobial compound(s).

In some embodiments, regions in a film that contain antimicrobial compound(s) may be introduced into the film, e.g., by removing portions of the film or creating voids in the film that are subsequently filled with a molten filler (e.g., a highly plasticized gelatin) that contains the antimicrobial compound(s). Different shaped and/or sized voids (e.g., windows, textures, sponge-like voids, etc.) may be created in or introduced into a film or layer of film (e.g., for films that include 2, 3, 4, or more layers) as desired. Several methods for creating voids in films that may be used to generate voids in a film that can subsequently be filled with molten bioactive fillers may be used with the present invention. For example, in some embodiments, fillers such as salts or sugars may be added to a film and subsequently dissolved away, leaving behind voids that may subsequently be filled with a composition (e.g., highly plasticized gelatin) containing the antimicrobial compound(s).

VI. METHOD FOR INCREASING THE WORKING TIMES OF THE FILMS

In some cases it may be desirable to reposition implants comprising or covered in an antimicrobial film of the present invention following initial placement in the body of a subject or human patient. In some embodiments, it may be desirable for films to retain their solid properties for several minutes to as long as 1 hour to allow for implant repositioning prior to liquefying. As used herein, the "working time" of a film generally refers to the amount of time that the film may be handled for before it becomes substantially liquefied; thus, films may exhibit longer working times, e.g., by exhibiting slower melting or liquefaction at a given temperature (e.g., body temperature) and/or increased toughness. Liquefaction can involve the combined process of melting and hydration. The hydration properties of the implant material (e.g., a highly plasticized gelatin) may be affected by the hydrophilicity of the plasticizer, the hydrophilicity of the bioactive agents (e.g., if present in high concentrations), and degree of crosslinking. For example, greater crosslinking, for example increased dehydrothermal heat treatment, can result in stiffer (more resistant to deformation), tougher (e.g., less likely tear), and/or dryer materials; since hydration may be involved in the liquefaction process of a material, a decreased water content of the film or wrap can result in increased working times for the material, as the film may liquefy more slowly due to the decreased water content of the film or wrap material. Additional plasticizer may be included in the material, e.g., to reduce the stiffness with little or no increase in the degree of swelling of the material after insertion into a subject such as a human patient. In some embodiments and as shown in the below examples, a film, covering, or wrap of the present invention may have a working time of more than one hour.

The working times of an antimicrobial film of the present invention may be increased by lightly crosslinking the film. Crosslinking methods that may be used include, e.g., radiation, dehydrothermal heat treatment, and chemical crosslinking. Chemical crosslinking agents may be used to crosslink proteins using, e.g., carboxyl, carbonyl, sulfhydryl, amine or hydroxyl reactive agents. Homo bi (or poly) functional or hetero bi (or poly) functional agents can be used for crosslinking. In addition, enzymes can also be used for crosslinking. Common agents that may be used to promote crosslinking include, e.g., glutaraldehyde, di succinimide esters of N-hydroxy succinimide (NHS), such as polyethylene glycol NHS esters, carbo-diimide crosslinkers, maleimides, imidoesters, haloacetyls, pyridyl disulfides, hydrazides, glyoxals, sulfones, periodates, isocynates, ureas, disulfides. Activatable crosslinkers, such as photoactivated crosslinkers, can also be used including psoralens, aryl azides or diazirines. Radiation and dehydrothermal treatment may be preferably used in some embodiments, as they offer the benefit of not needing to introduce new chemical agents into the films.

Crosslinking of a film may in some embodiments preferably be performed prior to adding antimicrobial compound (s) to the film, since crosslinking can potentially adversely affect antimicrobial compound(s) in the film. For example, the heat associated with dehydrothermal crosslinking treatment can have undesirable impacts on the stability and residual activity of bioactive agents such as minocycline, rifampin, MeSNA, fatty acids or glycerol nitrates. Similarly, chemical crosslinking agents or radiation may react with bioactive agents. As shown in the below examples, different designs allow incorporation of bioactive agents into the films subsequent to partial crosslinking. For example, preformed pockets may be created in a film that allows for addition of bioactive agents, e.g., comprised in a formulation with a shorter working time such as, e.g., a gelatin formulation or a highly plasticized gelatin with a shorter working time, or in another liquid or solid formulation. As shown in the below examples, the working time and flexibility of films can be adjusted by the duration and temperature of dehydrothermal treatment, and the ductility can be affected by adjusting the quantity of plasticizer and/or water remaining in the film.

VII. METHODS FOR REDUCING INFECTION

In various aspects the antimicrobial bioabsorbable films of the present invention may be used to reduce or prevent infection or other complications, such as capsular contracture, that may be associated with the implantation of a medical device, such as a breast implant. In some embodiments, infections associated with breast reconstruction, breast implants, and/or breast tissue expanders may be reduced or substantially prevented. The bioabsorbable films may also be used to wrap a portion or all of an implanted device. The wrapping may occur before or during a surgery. In various embodiments, other complications of implanted devices may be reduced or substantially prevented such as, e.g., fibrosis, scaring, and/or formation of adhesions.

The following methods are provided as examples for how a wrap, covering, or film of the present invention may be applied to an implant in a surgical pocket. In some embodiments, an implant is fully wrapped with the substantially solid film prior to inserting it into a surgical pocket. Alternately, the wrap can be applied to the implant by lining all or part of the surgical pocket with the film and then inserting the implant into a subject, such as a human patient. In some cases, the bottom or certain portions of the surgical pocket can be lined with film and then additional film is draped over the top and sides of the implant prior to insertion.

Application of a wrap, film, or covering of the present invention can also be accomplished by converting a solid film of the present invention into a plurality of particles or smaller pieces (e.g., that are substantially solid at room temperature and that liquefy in situ at body temperature, like the solid film). The particles may be formed by cryomilling the solid film (e.g., a solid gelatin film) or by other mechanical (e.g., chopping, mincing, dicing) processes. Particles can also be directly formed from the molten gelatin material by dripping, dispersing droplets or emulsifying in a non-solvent, such as an oil or silicone fluid, and then cooling to solidify. Particles can further be formed by extruding a molten gelatin into thin filaments that are chopped upon cooling. Particles can be directly molded by extruding the molten gelatin into molds with particle shapes or indentations and then cooling. Particles can be directly applied to the implant or in the surgical pocket prior to placement of an implant. Particles can also be suspended in a volatile non-solvent propellant and then sprayed. Examples of volatile non-solvent propellants are butane, propane, volatile dimethicones and cyclomethicones and hydrofluoroalkanes such as tetrafluoroethane, difluoroethane and hexafluoropropane. Particles can also be suspended in fluids that are absorbable, drain, or evaporate and spread in the surgical pocket or on the implant. Plasticizing agents such as aliphatic polyols, sugars, polyethylene glycols and glycerols, aqueous fluids and short chain or unsaturated lipids can be used to facilitate spreading. A plasticizing agent may be used instead of or in combination with a volatile non-solvent propellant.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Fabrication of Highly Plasticized-Gelatin Films

Molten gelatin was made by adding 16 g porcine gelatin to 40 ml water and dissolving at 80 C. 16 g glycerol was then stirred in to form a plasticized solution. This was poured into a large plate to form a thin layer of liquid at the bottom and allowed to cool. Upon cooling, the thin film solidified and was peeled off of the plate. It could be wrapped around a silicone breast implant to which it conformed and adhered. The film was placed in a 37 C incubator and checked periodically. It remained solid for approximately 10 minutes after which is became soft and melted to a viscous liquid indicating a working time of approximately 10 minutes to place the implant from the time it enters the body.

Example 2

Adhesive Layer on Highly Plasticized Gelatin Film

A film was formed as in Example 1. A separate solution of 8 g gelatin in 4 ml water was heated to which was added 2 ml 50% gluconic acid. This was poured on top of the plasticized gelatin film. Upon cooling the top surface of the plasticized gelatin film was now sticky and very adhesive.

Example 3

Production of Minocycline/Rifampin Disc 20 ml of plasticized gel was made as described in Example 1. To this was added 1.5 ml ethanol containing 20 mg Minocycline and 10 mg Rifampin. To form a coated test disc, molten plasticized-gel was pipetted into 24 well microtiter plates until the bottom of each well was covered (approximately 1-2 mm thick layer of liquid). A solid 2 mm thick, 6 mm diameter silicone disk (same material as breast implant shells are fabricated with) was placed on top and the plate cooled at room temperature for 2 minutes. The film+disk was briefly heated and another film layer (thickness of approximately 1-2 mm) was placed atop the disk. The gel was allowed to cool at room the ethanol to evaporate. Finally the film covered discs were removed from the mold and the layers were cut with a 7.5 mm diameter cork borer. This resulted in 7.5 mm test disc that was comprised of a 6 mm diameter silicon disc completely encased in antimicrobial gel wrap with 2 mm on each side of the disc. Films were also made using 2 mg Rifampin and 1 mg Minocycline.

Example 4

Production of Minocycline/Rifampin/GTN Disc

Another set of test discs were produced using the same method as in Example 3 except 10 mg Glyceryl Trinitrate was combined with the 20 mg Minocycline and 10 mg Rifampin in ethanol prior to being added to the molten plasticized gel. Films were also made where 10 mg Glyceryl Trinitrate was combined with 2 mg Rifampin and 1 mg Minocycline.

Example 5

Test to Determine Antimicrobial Efficacy

Both test discs and control silicone discs were independently exposed to 1 mL of $5.5 \times 10^5$ CFU of various test microorganisms including methicillin resistant *Staphylococcus aureus, Staphylococcus epidermidis*, and multidrug resistant *Pseudomonas aeruginosa* and incubated for 24 hrs at 37 C. Discs were then removed from their fluid wells and washed for 30 min shaking in 0.9% sterile saline. To disrupt biofilm, discs were then placed in 5 mL of 0.9% sterile saline and sonicated for 15 minutes. Resulting solution was quantitative cultured by serial dilution and pipetted onto tyrpticase soy agar with 5% sheep blood, incubated for 24 hrs and counted for growth. Tests were performed in Triplicate. Means and Standard deviations are presented in the plots below for challenges with clinical strains of methicillin resistant *staphylococcus aureus* (MRSA), *Pseudomonas aeruginosa* and *Klebsiela pneumonia*. Results are shown in FIG. 1.

The films with 1 mg/ml Minocycline and 0.5 mg/ml Rifampin were able to prevent the gram positive and gram negative organisms tested from adhering to the silicone. GTN worked synergistically with lower doses of Minocycline (0.05 mg/ml) and Rifampin (0.1 mg/ml) to protect the silicone from bacterial colonization.

Example 6

Production of Minocycline/Rifampin/MeSNA Test Disc

Another set of test discs were produced using the same method as in Example 3. 1000 mg of sodium mercaptoethane sulfonate (MeSNA) was added to the 20 ml molten plasticized gel in addition to 2 mg Minocycline and 1 mg Rifampin (low dose M/R) prior to casting. To test synergy, control disks consisting of MeSNA alone, Minocycline/Rifampin alone and disks with no additives were formed as well.

Example 7

Antimicrobial Testing

Figure 3:
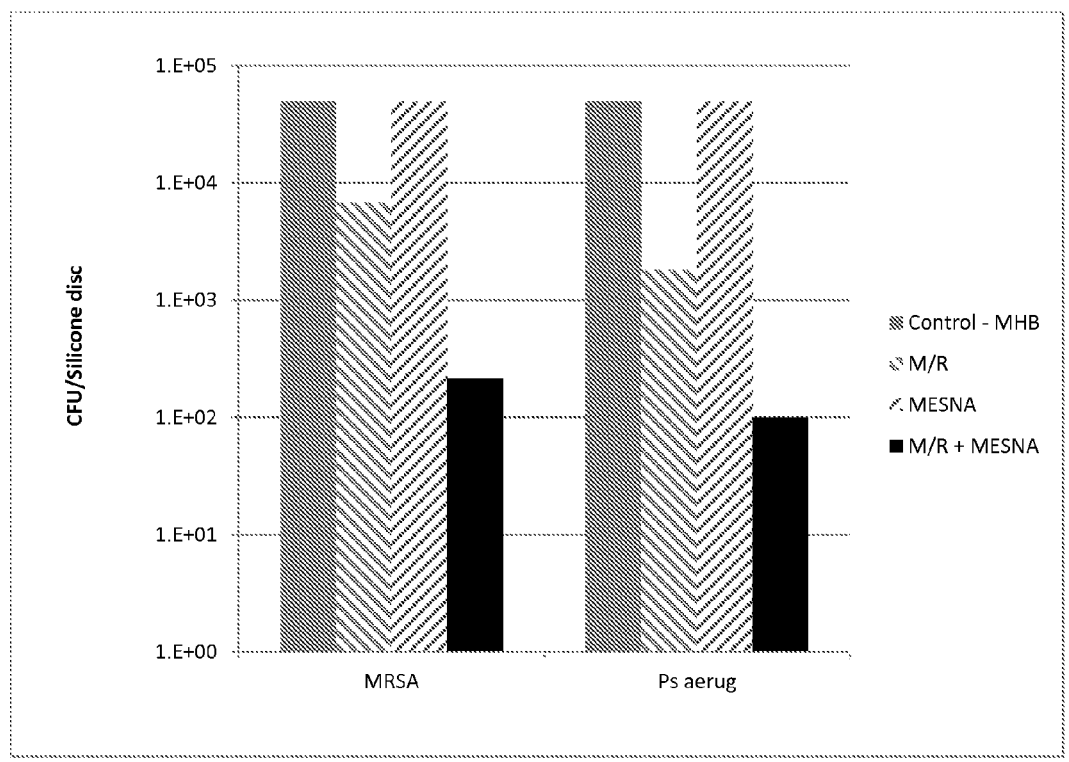
FIG. 3: Inhibition of clinical strains of MRSA and *Pseudomonas aeruginosa*. The presence or absence of minocycline and rifampin (M/R), GTN, and/or MeSNA is shown.

Testing was performed as in Example 5 utilizing clinical strains of MRSA and *Pseudomonas aeruginosa* to challenge. Quantitative recoveries are shown in FIG. 3.

The combination of MeSNA and low dose M/R reduced adherence of MRSA and *Pseudomonas aeruginosa* over 1 log below either alone.

Example 8

M/R+MeSNA+GTN Discs

Additional discs were made as in Example 6. In addition to MeSNA and M/R, GTN was included as in Example 4.

Example 9

Testing of M/R+MeSNA+GTN Discs

Figure 4:
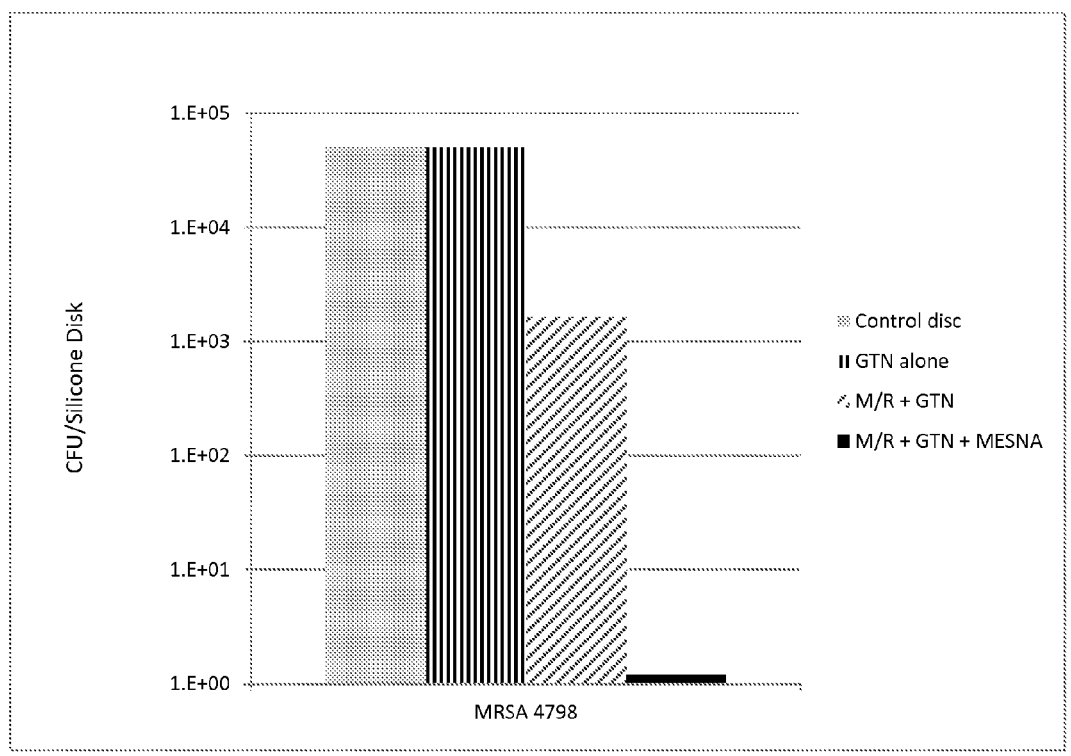
FIG. 4: Inhibition of a clinical isolate of MRSA on silicone discs. The presence or absence of minocycline and rifampin (M/R), GTN, and/or MeSNA is shown.

Testing was performed as in Example 6 utilizing a clinical isolate of MRSA to challenge. Quantitative recoveries for GTN alone, GTN+M/R and GTN+M/R+MeSNA are shown in FIG. 4. MeSNA alone, M/R alone and M/R+MeSNA results are reported in Example 7.

Results are shown in FIG. 4. Only the M/R+GTN+MeSNA was able to completely prevent colonization of the disk surface.

Example 10

M/R+MeSNA+Caprylic Acid Discs

Additional discs were made as in Example 6. In addition to MeSNA and M/R, Caprylic acid at a concentration of 10 mg/ml was included as in Example 4.

Example 11

Testing of M/R+MeSNA+GTN Discs

Testing was performed as in Example 6 utilizing a clinical isolate of *Pseudomonas aeruginosa* to challenge. Quantitative recoveries for M/R alone, MeSNA alone, Caprylic acid alone and the combinations MeSNA+M/R and Caprylic acid+MeSNA+M/R GTN+M/R are shown in FIG. 5.

Figure 5:
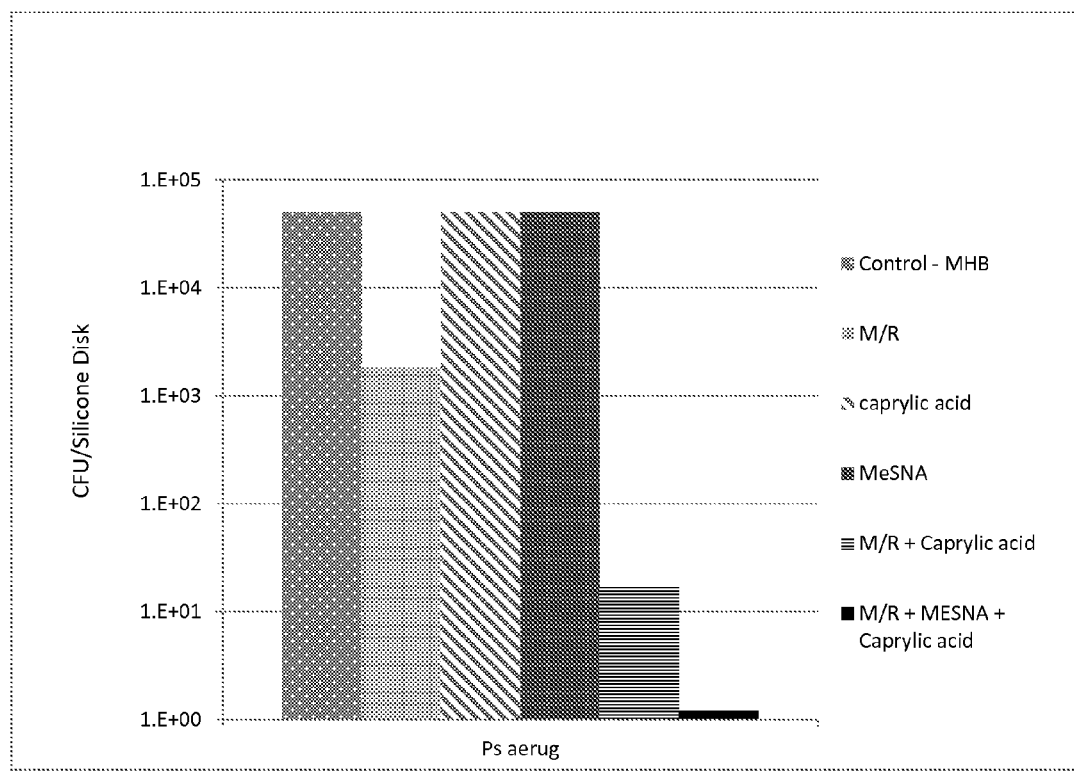
FIG. 5: Inhibition of a clinical strain of Pseudomonas aeruginosa. The presence or absence of minocycline and rifampin (M/R), MeSNA, and/or caprylic acid is shown.

Results are shown in FIG. 5. Only the (M/R+MeSNA+Caprylic acid) was able to completely prevent colonization of the disk surface.

Example 12

Method for Assessing Working Times Prior to Melting

The following method for assessing working times prior to melting was used in following examples. Working times of solid films were assessed by compressing both sides against thick gauze soaked with saline and incubating for specified times at 37 C. The gauze was pre-incubated at 37° C. prior to contacting with the films. Following the incubation interval, the films were removed and tensile strength was assessed by manually stretching the film to more than 110% of its original length and observing whether the film tore or recoiled.

Example 13

Increased Working Time by Dehydrothermal Heat Treatment

A highly plasticized gelatin film was prepared as in Example 1. The film was heated in an oven at 175° F. for 2 hours. Following cooling, the working time of the film was assessed as previously described. The film had a working time of approximately 15 minutes.

Example 14

Further Increased Working Time by Dehydrothermal Heat Treatment

A highly plasticized gelatin film was prepared as in Example 1. The film was heated in an oven at 175° F. for 2 hours and subsequently at 225° F. for 4 hours. Following cooling, the working time of the film was assessed. The film had a working time of more than 1 hour. This film was noticeably stiffer prior to assessment of working time. During the working time assessment, the film absorbed moisture and increased in flexibility. Flexibility of the solid film could be restored following removal from the oven by allowing exposure to ambient humid air.

Example 15

Increased Working Time with Increased Ductility

A highly plasticized molten gelatin solution was prepared by combining 4 g porcine gelatin, 4.8 g glycerol and adding water to 20 ml total volume at 80° C. The molten solution was cast onto a tray and placed in an oven at 175° F. for 8 hours. Subsequently the temperature was increased to 225° F. for 4 hours. Following cooling, the film was more flexible than in the previous example. This working time of this film was assessed as previously described. This film had a working time of more than 1 hour.

As shown here, the working time and flexibility of films can be adjusted by the duration and temperature of dehydrothermal treatment, as well as by the quantity of plasticizer and/or water remaining in the film.

Example 16

Figure 6:
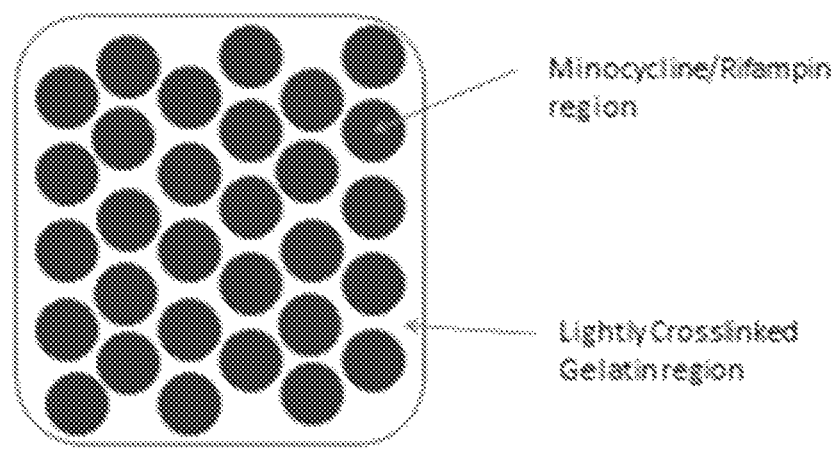
FIG. 6: A drawing of a film design containing structural regions of lightly crosslinked gelatin and regions with Minocycline/Rifampin.

Open Partially Crosslinked Gelatin Film Containing Regions of Minocycline/Rifampin in Non-Crosslinked Gelatin A highly plasticized molten gelatin solution was prepared by combining 4 g porcine gelatin, 4.8 g glycerol and adding water to 20 ml total volume at 80° C. The molten solution was cast onto a tray in a thin layer and placed in an oven at 175° F. for 8 hours. The film was subsequently cured for 4 hours at 225° F. The resulting film was removed and holes were punched out such that more than 50% of the surface contained voids. Molten gelatin containing Minocycline and Rifampin was prepared as in Example 3 and cast on top of the void containing layer of film. It was compression molded to fill in the voids and then allowed to cool. The resulting film was tested for working time. The structural portion of the film retained a working time of 1 hour but was weaker than the continuous similar film. The antimicrobial portion melted earlier, as compared to Example 15, and minocycline and rifampin began to elute from the film by one hour. A drawing of a film design containing structural regions of lightly crosslinked gelatin and regions with Minocycline/Rifampin is shown in FIG. 6.

Example 17

Open Laminate Partially Crosslinked Gelatin Film Containing Regions of Minocycline/Rifampin in Non-Crosslinked Gelatin A highly plasticized molten gelatin solution was prepared by combining 4 g porcine gelatin, 4.8 g glycerol and adding water to 20 ml total volume at 80° C. The molten solution was cast onto a tray in a thin layer and placed in an oven at 175° F. for 8 hours. The resulting film was removed and holes were punched out such that more than 50% of the surface contained voids. The film with the voids was placed on top of a continuous thin film prepared in an analogous manner except without holes punched out. The 2 layer laminate was subsequently further cured at 225° F. for 4 hours then removed and allowed to cure. Molten gelatin containing Minocycline and Rifampin was prepared as in Example 3 and cast on top of the void containing layer of the cool 2-layer film. It was compression molded to fill in the voids and then allowed to cool. Following cooling the resulting film was tested for working time. There was 1 hour working time and with no delamination of the two structural layers. The tensile strength of the laminate was greater than in the previous example. The antimicrobial regions melted before the structural part. As long as the continuous layer was on bottom the antimicrobial region did not flow out of the film.

Example 18

Figure 7:
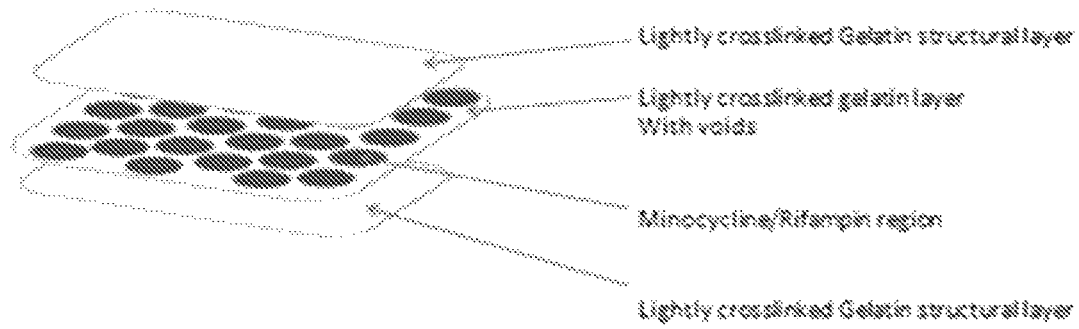
FIG. 7: Example of a 3-layer laminate film containing a middle layer comprising antimicrobial compounds.

Closed Laminate Partially Crosslinked Gelatin Film Containing Regions of Minocycline/Rifampin in Non-Crosslinked Gelatin A highly plasticized molten gelatin solution was prepared by combining 4 g porcine gelatin, 4.8 g glycerol and adding water to 20 ml total volume at 80° C. The molten solution was cast onto a tray in a thin layer and placed in an oven at 175° F. for 8 hours. The resulting film was removed and holes were punched out such that more than 50% of the surface contained voids. The film with the voids was placed on top of a continuous thin film prepared in an analogous manner except without holes punched out. Then a continuous film was placed on top of the open side. The 3 layer laminate was subsequently further cured at 225° F. for 4 hours then removed and allowed to cure. Molten gelatin containing Minocycline and Rifampin was prepared as in Example 3 and injected through a short needle into the void spaces in the middle of the cool 3-layer film. It was then allowed to cool. Following cooling the resulting film was tested for working time. There was 1 hour working time and with no delamination of the three structural layers. The enclosed laminated fully contained the antimicrobial regions during the working time assessment. This design is illustrated in FIG. 7.

It will be apparent to one of ordinary skill in the art that different shape and size voids (including windows) could be used in these laminate constructs. Other methods of creating voids in films exist that may be used to generate voids in a film that can subsequently be filled with molten bioactive fillers. One is to add fillers such as salts or sugars that can be subsequently dissolved away, leaving behind voids.

Example 19

3-Layer Sandwich Laminate

A highly plasticized molten gelatin solution was prepared by combining 4 g porcine gelatin, 4.8 g glycerol and adding water to 20 ml total volume at 80° C. The molten solution was cast onto a tray and placed in an oven at 175° F. for 8 hours. Subsequently the temperature was increased to 225° F. for 4 hours, the film removed and allowed to cool. Molten gelatin containing Minocycline and Rifampin was prepared as in Example 3 and poured on top of a thin film of crosslinked gelatin. A second film of crosslinked gelatin was placed on top and the middle layer was compression molded into a thin film between the outer layers. The laminate was allowed to cool forming a solid film.

Example 20

Single Layer Reinforced Film

A highly plasticized molten gelatin solution was prepared by combining 4 g porcine gelatin, 4.8 g glycerol and adding water to 20 ml total volume at 80° C. The molten solution was extruded into filaments that were placed onto a tray which was placed in an oven at 175° F. for 8 hours. Subsequently the temperature was increased to 225° F. for 4 hours, the filaments removed and allowed to cool. The filaments were lain across one another as a dense mat. Molten gelatin containing Minocycline and Rifampin was prepared as in Example 3 and compression molded into the mat of filaments. The film was allowed to cool forming a meltable filament reinforced film.

Example 21

Filled Sponge

A highly plasticized molten gelatin solution was prepared by combining 4 g porcine gelatin, 4.8 g glycerol and adding water to 20 ml total volume at 80° C. Cellulose acetate particles were dispersed to form a dense suspension. Molten suspension was compressed into a film onto a tray and placed in an oven at 175° F. for 8 hours. Subsequently the temperature was increased to 225° F. for 4 hours, the film removed and allowed to cool. The film was then immersed in acetone solution dissolving away the particles and leaving a sponge. The sponge was rinsed and allowed to fully dry. Molten gelatin containing Minocycline and Rifampin was prepared as in Example 3 and injected through a needle into the sponge filling the interstices. The filled sponge was allowed to cool.

A highly plasticized molten gelatin solution was prepared by combining 4 g porcine gelatin, 4.8 g glycerol and adding water to 20 ml total volume at 80° C. Ethyl cellulose particles were dispersed to form a dense suspension. Molten suspension was compressed into a film onto a tray and placed in an oven at 175° F. for 8 hours. Subsequently the temperature was increased to 225° F. for 4 hours, the film removed and allowed to cool. The film was then immersed in diluted acetone solution dissolving away the particles and leaving a sponge. The sponge was allowed to fully dry. Molten gelatin containing Minocycline and Rifampin was prepared as in Example 3 and injected through a needle into the sponge filling the interstices. The filled sponge was allowed to cool.

Example 22

Wrap Cytotoxicity Testing

Preparation of Solid Film Wraps

Silicone discs covered with plasticized gelatin films were formed as in Example 3. High concentration Minocycline (M) and Rifampin (R) films were created with a final concentration of 0.1% M and 0.05% R (high M/R), while low concentration M/R films were created with 0.01% M and 0.005% R (low M/R). In some experiments, MESNA was also added to a final concentration of 5%.

Cytotoxicity Tests

A human fibroblast (HEK-293T) cell-line was maintained in Dulbecco's modified Eagle's medium (DMEM) (MediaTech Inc., Manassas, Va.) supplemented with 10% heat-inactivated fetal bovine serum (FBS) (Sigma Co., St. Louis, Mo.), in 5% $CO_2$ at 37° C. 293T cells were passaged twice per week. Cells were plated at a density of $5 \times 10^5$ cells/well in 48-well culture plates using a cell counter (Z1 Coulter Particle Counter, Beckman Coulter). At 50% confluence, discs wrapped with the previously described combinations of M, R and MeSNA were added into the wells. Gelatin wrapped discs (no antimicrobial agents) and medium were used controls. After 24 hrs, drug induced cell viability and toxicity was assessed by Alamar blue and MTT (3-[4,5-dimethylthiazol-2-yl]-2,5-diphenyltetrazolium bromide) assays respectively.

1. Alamar Blue Assay:

Alamar blue assay (Life Technologies Corp., Carlsbad, Calif.) was performed to assess sensitivity of the drug impregnated gelatin discs to cells. This assay is based on reduction of the indicator dye, resazurin, to the highly fluorescent resorufin in corresponding to metabolically active cells. Drug sensitized cells rapidly lose their metabolic capacity in the reduction of resazurin and thus produce no fluorescent signal. Briefly, after 24 hr of treatment, plate was centrifuged and medium was replaced with DMEM+5% FBS without phenol red. Alamar blue reagent (50 ul) was directly added to cells in the culture medium and incubated for 3 hr at 37° C. Absorbance was determined at 570 nm using UV visible spectrophotometer (BioTek Instruments, Inc., Winooski, Vt.). Inhibition of cell viability was compared with untreated control cells. Results are expressed as percentage of survival normalized to untreated controls. All experiments were performed in triplicate.

2. MTT Assay:

In vitro cytotoxicity was assessed quantitatively by monitoring the mitochondrial reduction activity of viable cells using the MTT assay (Sigma Co., St. Louis, Mo.). The bioactive agent treatment protocol followed in the Alamar blue assay was followed here as well. After 24 hr of treatment, plates were centrifuged and medium was replaced with DMEM+5% FCS without phenol red. MTT solution was added to 10% of the culture medium and incubated at 37° C. for 3 hr. MTT solvent was added to dissolve formazan crystals and absorbance of the dissolved materials was measured at 570 nm spectrometrically using a UV Vis spectrophotometer (BioTek Instruments, Inc., Winooski, Vt.). Bioactive agent induced toxicity from treated cells were determined by comparison of signals from untreated control cells. Results are expressed as percentage of surviving cells relative to controls. Experiments were performed in triplicate.

As shown in FIGS. 8A-B, the control gelatin wrapped disks had no adverse effect on the viability of 293T cells relative to cells grown in broth. From both the Alamar blue (FIG. 8A) and MTT assays (FIG. 8B), gelatin wrapped disks containing MeSNA, Low M/R, High M/R and MeSNA+Low M/R did not produce a significant reduction in cell viability compared to cells grown in broth (P=0.74). Results are shown in FIG. 8.

Example 23

Antimicrobial Crosslinked Wrap Made by Method of Soaking Crosslinked Wrap in Antibiotic Solution then Drying A highly plasticized molten gelatin solution was prepared by combining 4 g porcine gelatin, 4.8 g glycerol and adding water to 20 ml total volume at 80° C. The molten solution was cast onto a tray in a thin layer and placed in an oven at 175° F. for 8 hours. The film was subsequently cured for 2 hours at 225° F. to dehydrothermally crosslink it and it was allowed to cool. 20 mg Minocycline and 10 mg Rifampin was dissolved in 1 ml ethanol. The volume was increased to 20 ml by adding water. A thin coating of solution was layered on top of the film. The film absorbed some of the liquid and turned orange reflecting absorption of the antibiotics. Excess liquid was poured off and the film was allowed to evaporatively dry. The antibiotic-loaded crosslinked wrap returned to its original thickness and retained its original ductility but had texturing on the surface of the solution side.

Example 24

Method of Extending Release from Antimicrobial Crosslinked Wrap Made by Method of Soaking Crosslinked Wrap in Antibiotic Solution then Drying then Further Heat Treating A highly plasticized molten gelatin solution was prepared by combining 4 g porcine gelatin, 4.8 g glycerol and adding water to 20 ml total volume at 80° C. The molten solution was cast onto a tray in a thin layer and placed in an oven at 175° F. for 8 hours. The film was subsequently cured for 2 hours at 225° F. to dehydrothermally crosslink it and it was allowed to cool. 40 mg Minocycline and 20 mg Rifampin was dissolved in 1 ml ethanol. The volume was increased to 20 ml by adding water. A thin coating of solution layered on top of the film. The film absorbed some of the liquid and turned orange reflecting absorption of the antibiotics. Excess liquid was poured off and the film was allowed to evaporatively dry. A 1 inch square of film was placed in petri dish. A second 1 inch square piece from the remaining dry film was further heat treated at 60° C. for 4 hr and then cooled. This was placed in a separate Petri dish. 10 m saline was added to both petri dishes which were incubated at 37° C. for 2 hours. Absorbance at 550 nm was read using a spectrophotometer. The liquid from the 60° C. heat treated sample had less absorbance than the other and the remaining film retained more color intensity.

Example 25

Antimicrobial 2-Layer Wrap Made by Method of Coating Crosslinked Wrap in Antibiotic Gelatin Solution A highly plasticized molten gelatin solution was prepared by combining 4 g porcine gelatin, 4.8 g glycerol and adding water to 20 ml total volume at 80° C. The molten solution was cast onto a tray in a thin layer and placed in an oven at 175° F. for 8 hours. The film was subsequently cured for 2 hours at 225° F. to dehydrothermally crosslink it and it was allowed to cool. 40 mg Minocycline and 20 mg Rifampin was dissolved in 1 ml ethanol. This was added to 19 ml of 30% gelatin/glycerol with a gelatin:glycerol ratio of 50:50. A thin coating of solution was spread on top of a prewarmed film (45° C.). The film absorbed some of the liquid and turned orange reflecting absorption of the antibiotics. The film set and was allowed to evaporatively dry. The coated, antibiotic-loaded crosslinked wrap retained its original ductility. A thin layer of coating solution was also spread on a crosslinked film from the previous example which had been preloaded with antibiotics. The coated film cooled and was allowed to evaporatively dry where it retained its original ductility.

Example 26

Antimicrobial 3-Layer Sandwich Laminate Made by Heat Sealing Edges

A highly plasticized molten gelatin solution was prepared by combining 8 g porcine gelatin, 9.6 g glycerol and adding water to 40 ml total volume at 80° C. The molten solution was cast onto 2 trays and placed in an oven at 175° F. for 8 hours. Subsequently the temperature was increased to 225° F. for 2 hours, the film removed and allowed to cool. Molten gelatin containing Minocycline and Rifampin was prepared as in Example 3 and a volume poured on top of a thin film of crosslinked gelatin. A second film of crosslinked gelatin was placed on top and the middle layer was compression molded into a thin film such that the outer layers extended beyond the edges of the antibiotic-containing middle layer which overlapped each other. The laminate was allowed to cool. Focused high intensity heat was applied using a heat gun to the overlapping edges of the non-antibiotic layers until they welded together forming a seal all around the circumference.

Example 27

Method of Application of Wrap to Transcutaneous Devices on Both Internal and External Surfaces Surgical drains are examples of transcutaneous devices that have portions on the subcutaneous side as well as the epidermal side of the skin. The subcutaneous side of the drain can be wrapped prior to closure of the surgical site and following closure the external side can be wrapped and secured with an adhesive dressing. Alternatively, the wrap can be applied to the skin round the exit site and secured with a dressing.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A biodegradable covering for a medical implant, the covering comprising a highly plasticized gelatin and at least one drug to reduce infection or capsular contraction, wherein the plasticized gelatin has a melting temperature of less than 38° C., and wherein the plasticized gelatin consists essentially of gelatin and from greater than 40% to about 60% plasticizer.

2. The covering of claim 1, wherein the plasticized gelatin has a melting temperature of 27-37° C.

3. The covering of claim 1, wherein the plasticized gelatin has a melting temperature of 30-37° C.

4. The covering of claim 2, wherein the plasticized gelatin comprises about 50-55% plasticizer.

5. The covering of claim 4, wherein the plasticizer is glycerol, a propylene glycol, a sugar, a carbohydrate, an amino acid, a salt, an acid, or a polyol.

6. The covering of claim 5 wherein the plasticizer is glycerol.

7. A biodegradable covering for a medical implant, the covering comprising a highly plasticized gelatin and at least one drug to reduce infection or capsular contraction, wherein the plasticized gelatin has a melting temperature of less than 38° C., wherein at least a portion of a surface of the covering has been treated with a gluconic acid solution.

8. The covering of claim 1, wherein at least a portion of a surface of the covering has been treated with a glycerol-gelatin liquid comprising about 60-90% glycerol or a solution comprising a carbohydrate, a starch, or a sugar.

9. The covering of claim 1, wherein the covering is sufficient in size or shaped to cover a breast implant.

10. The covering of claim 9, wherein the covering is shaped as a film, a wrap, a pouch or a bag.

11. A biodegradable covering for a medical implant, the covering comprising a highly plasticized gelatin and at least one drug to reduce infection or capsular contraction, wherein the plasticized gelatin has a melting temperature of less than 38° C.; wherein the covering is sufficient in size or shaped to cover a breast implant; wherein the covering is shaped as a film, a wrap, a pouch or a bag; and wherein the covering is a pouch or a bag; wherein the covering has a central region and a plurality of lateral appendages, or the covering is substantially star-shaped.

12. The covering of claim 1, wherein the covering comprises a plurality of biodegradable layers.

13. The covering of claim 1, wherein the at least one drug is selected from the group consisting of an antimicrobial agent, an anti-inflammatory agent, an anti-scarring agent, a hemostatic agent, an anti-neoplastic agent, a calcium channel blocker, and a leukotriene inhibitor.

14. The covering of claim 13, wherein the at least one drug is an antimicrobial agent.

15. The covering of claim 14, wherein the antimicrobial agent is bacitracin, cephalexin, gentamicin, an antiseptic, a chelator, chlorhexidine, gendine, gardine, a leukotriene inhibitor, hydrogen peroxide, a nitroglycerin, or a nitric oxide donor.

16. The covering of claim 1, wherein the covering comprises at least one of mercaptoethane sulfonate (MeSNA), minocycline, rifampin, or glyceryl trinitrate (GTN).

17. The covering of claim 16, wherein the covering comprises at least two of mercaptoethane sulfonate (MeSNA), minocycline, rifampin, and/or glyceryl trinitrate (GTN).

18. The covering of claim 17, wherein the covering comprises minocycline, rifampin, and mercaptoethane sulfonate.

19. A biodegradable covering for a medical implant, the covering comprising a highly plasticized gelatin and at least one drug to reduce infection or capsular contraction, wherein the plasticized gelatin has a melting temperature of less than 38° C.; wherein the covering comprises minocycline, rifampin, and mercaptoethane sulfonate; and wherein the covering further comprises glyceryl trinitrate (GTN), a monoglyceride, or a fatty acid.

20. The covering of claim 19, wherein the fatty acid is a $C_{6-12}$ alkanoic acid.

21. The covering of claim 20, wherein the fatty acid is caprylic acid (octanoic acid).

22. The covering of claim 19, wherein the covering further comprises glyceryl trinitrate (GTN) and caprylic acid.

23. The covering of claim 1, wherein at least a portion of the covering has been exposed to crosslinking.

24. A biodegradable covering for a medical implant, the covering comprising a highly plasticized gelatin and at least one drug to reduce infection or capsular contraction, wherein the plasticized gelatin has a melting temperature of less than 38° C.; wherein at least a portion of the covering has been exposed to crosslinking; and wherein the covering comprises regions that have been exposed to crosslinking and regions that have not been exposed to crosslinking.

25. The covering of claim 24, wherein the regions that have not been exposed to crosslinking comprise minocycline, rifampin, glyceryl trinitrate (GTN), mercaptoethane sulfonate (MeSNA), or caprylic acid.

26. The covering of claim 1, wherein the covering comprises multiple layers.

27. A biodegradable covering for a medical implant, the covering comprising a highly plasticized gelatin and at least one drug to reduce infection or capsular contraction, wherein the plasticized gelatin has a melting temperature of less than 38° C.; wherein the covering comprises multiple layers; and wherein the covering comprises a first layer comprising a partially crosslinked plasticized gelatin and a second layer comprising a plasticized gelatin that has not been crosslinked, wherein the second layer comprises the drug.

28. A biodegradable covering for a medical implant, the covering comprising a highly plasticized gelatin and at least one drug to reduce infection or capsular contraction, wherein the plasticized gelatin has a melting temperature of less than 38° C.; wherein the highly plasticized gelatin is comprised on an adhesive backing.

29. A kit comprising a breast implant and the biodegradable covering of claim 1.

30. A breast implant assembly comprising a biodegradable covering of claim 1 containing a breast implant.

31. A method for reducing at least one post-surgical indication from breast augmentation or breast reconstruction in a subject, the method comprising surgically implanting into the subject the breast implant assembly of claim 30.

32. A transcutaneous device assembly comprising a biodegradable covering of claim 1 that is wrapped around at least a portion of the transcutaneous device.

33. A method for reducing at least one post-surgical indication from implantation of a transcutaneous device in a subject, the method comprising surgically implanting into the subject the transcutaneous device assembly of claim 32.

* * * * *